Feb. 13, 1940. W. KORDES Plant Pat. 363
ROSE PLANT
Filed June 1, 1939
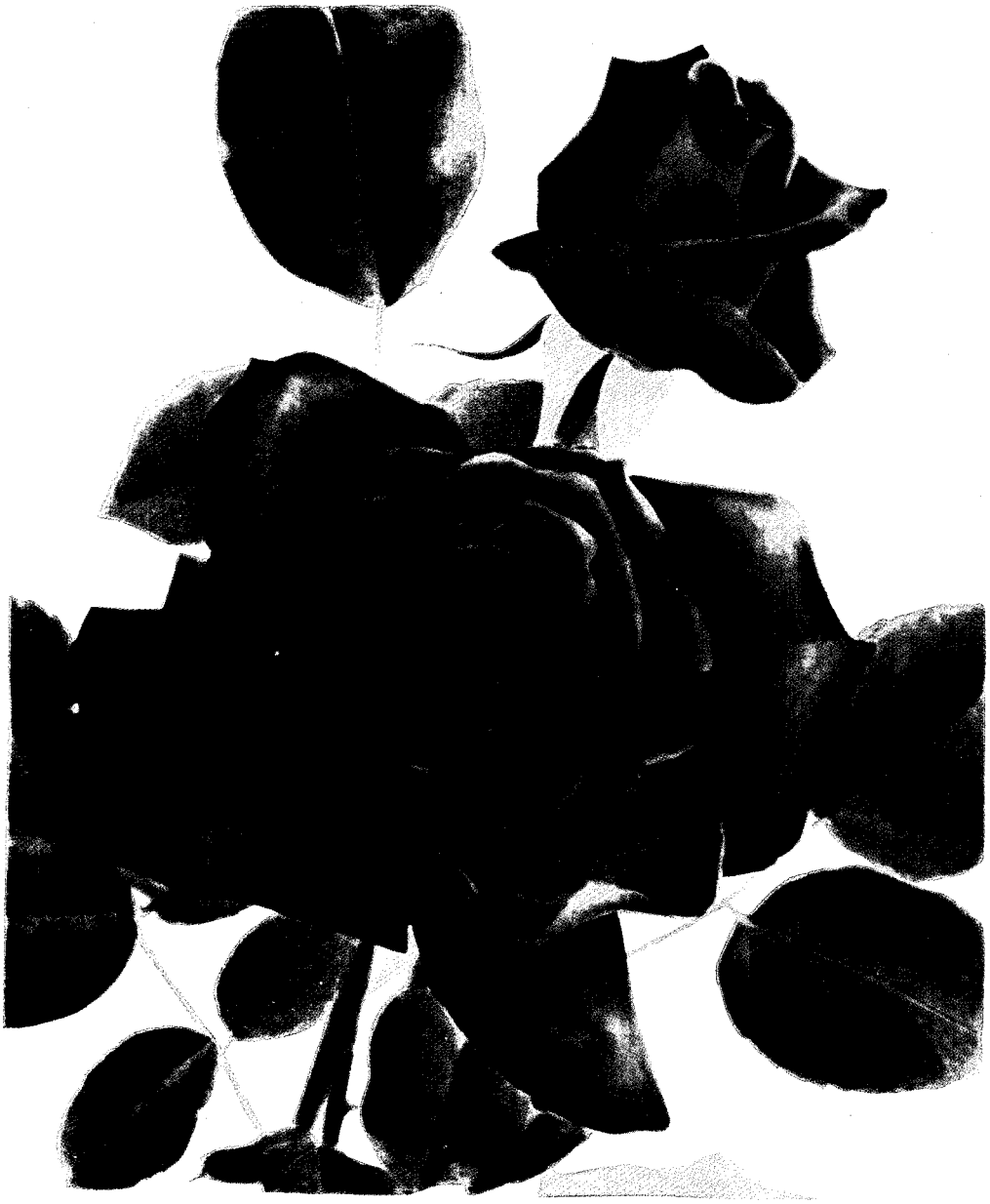
Inventor
W. Kordes
By Robb & Robb
Attorneys Patented Feb. 13, 1940

Plant Pat. 363

UNITED STATES PATENT OFFICE

363

ROSE PLANT

Wilhelm Kordes, Sparrieshoop in Holstein, Germany, assignor to Jackson & Perkins Company, Newark, N. Y.

Application June 1, 1939, Serial No. 276,920

1 Claim. (Cl. 47—61)

The present invention relates to a new and distinct variety of rose plant produced by crossing of certain known varieties having desirable characteristics of particular value in the combination obtained.

Of primary importance to the combination is the depth of color of the blossoms, a very dark Maroon to Ox-blood Red, persisting to the very end of the flowering. When the sepals first divide, the buds present the Maroon color, and when half opened the coloring appears as Burnt Lake to Maroon, which with the thick petals, satiny on the inside and shiny on the outside, makes for distinct attractiveness of the rose.

In addition to the foregoing, the large size of the flower,—approximately five inches in diameter,—and the average petalage of 35, are notable features.

These flowers mostly individual and high centered are borne on medium length strong stems, and retain their form to the end.

The young foliage of the plant is of Hay's Maroon on the upper side while the new wood is Vandyke Red and the old wood Cress Green color, thus producing a subdued and dignified color combination.

This new rose has been asexually reproduced and its characteristics as stated found to be fixed.

The following is a detailed description of the new variety, the color terminology being in accord with Ridgway's color standard:

Parentage:

*Seed parent.*—Catherine Kordes x E. G. Hill.
*Pollen parent.*—Fritz Hoger.

Classification:

*Botanic.*—Hybrid Tea.
*Commercial.*—Hybrid Tea.

*Flower*

Blooming habit:

Observations made in the morning of June 30, 1938, at Newark, New York.
Blooms once.
Recurrent—intermittent.

Bud:

*Size.*—Large.
*Form.*—Long, pointed. Unaffected by wet or hot weather.
*Color.*—When sepals first divide—Maroon, Plate I. When petals begin to unfurl—between Burnt Lake, Plate 12, and Maroon, Plate I. When half blown: inside of petals—Maroon, Plate I; reverse of petals—Ox-blood Red, Plate I.
*Sepals.*—Smooth edge. Curl back when bud begins to unfurl.
*Calyx.*—Shape—apple. Size—broad. Aspect—smooth.
*Peduncle.*—Length—medium. Aspect—smooth. Color—Pompeian Red, Plate 13, together with Cress Green, Plate 31. Strength—stiff, heavy.
*Opening.*—Bud opens well. Is not affected by adverse conditions.

Bloom:

*Size.*—Large. Average size when fully expanded—5″.
*Borne.*—Several together.
*Stems.*—Medium length, normal strength.
*Form.*—When first open—high center. Retains its form to the end.
*Petalage.*—Double (full but open center). Number of petals under normal conditions—35.
*Color.*—Center of flower, between Maroon and Ox-blood Red, Plate I. Outer petals—between Maroon and Ox-blood Red, Plate I. Base of petals (aiglet)—very small, Baryta Yellow, Plate 4. Inside of petals—between Maroon and Ox-blood Red, Plate I. Reverse of petals—Ox-blood Red, Plate I. General tonality from a distance—Velvety Dark Red.
*Discoloration.*—At end of first day—Maroon and Ox-blood Red, Plate I. Second day—Maroon and Ox-blood Red, Plate I. Third day—Ox-blood Red, Plate I.

Petals:

*Texture.*—Thick. Unaffected by wet or hot weather.
*Appearance.*—Inside—satiny. Outside—Shiny.
*Form.*—Oval, pointed.
*Arrangement.*—Imbricated (regularly arranged shingle-like). Petaloids in center—few, small.
*Persistence.*—Drop off cleanly.
*Fragrance.*—Moderate. Nature—"Old Rose perfume" (Centifolia).
*Lasting quality.*—On the plant—long. As cut flower—fair.

Genital organs:

*Stamens, anthers.*—Medium size. Color—Yellow Ocher, Plate 15. Arrangement—regular round styles.
*Stamens, filaments (threads).*—Medium length. Color—Light Jasper Red, Plate 13.
*Pollen.*—Ochraceous Orange, Plate 15.
*Styles.*—Bunched, medium length, heavy.

*Stigmas.*—Color, Lemon Chrome, Plate 4.
*Ovaries.*—All enclosed in calyx.

Fruit:
Variety is fertile with its own pollen.
*Form.*—Ovoid.
*Aspect.*—Smooth.
*Sepals.*—Permanent; recurved.

*Plant*

Form:
Bush.

Growth:
Vigorous, upright.

Foliage:
*Number of leaflets.*—5 to 7.
*Size.*—Medium.
*Quantity.*—Normal.
*Color.*—New foliage: upper side—Hay's Maroon, Plate 13; under side—Vandyke Red, Plate 13. Old foliage: upper side—Dark Cress Green, Plate 31; under side—Light Cress Green, Plate 31.
*Shape.*—Oval.
*Texture.*—Upper side—leathery, corrugated. Under side—rough. Ribs and veins—prominent.
*Edge.*—Serrated (saw toothed).
*Serration.*—Double, small, sharp.
*Rachis.*—Color—Light Cress Green, Plate 31. Under side—smooth.
*Stipules.*—Medium length, smooth.
*Disease resistance.*—Resistant.

Wood:
*New wood.*—Color—Vandyke Red, Plate 13. Bark—smooth.
*Old wood.*—Color—Cress Green, Plate 31. Bark—smooth.

Thorns: (Thorns are divided into thorns, prickles and short needles.)
*Thorns.*—Quantity: on main stalks from base—ordinary; on laterals from stalk—few. Form—narrow base, short length, hooked downward. Color when young—Pompeian Red, Plate 13. Position—irregular.
*Prickles.*—Quantity: on main stalks—few; on laterals—few.

I claim:
A new and distinct variety of Hybrid Tea rose plant, characterized by the persistency of the dark Maroon color of its flowers, and the thick satiny-shiny appearing petals making up the high centered large size flowers borne on medium length strong stems, substantially as shown and described.

WILHELM KORDES.